United States Patent [19]

Inbasekaran et al.

[11] Patent Number: 4,885,403

[45] Date of Patent: Dec. 5, 1989

[54] PROCESS FOR MAKING PROPARGYL ETHERS OF BISPHENOLS

[75] Inventors: Muthiah N. Inbasekaran, Midland; Stoil K. Dirlikov, Ypsilanti, both of Mich.

[73] Assignee: The Dow Chemical Company, Midland, Mich.

[21] Appl. No.: 225,699

[22] Filed: Jul. 29, 1988

Related U.S. Application Data

[63] Continuation-in-part of Ser. No. 56,190, Jun. 1, 1987, abandoned.

[51] Int. Cl.$^4$ .................... C07C 41/00; C07C 43/20
[52] U.S. Cl. .................... 568/631; 568/23; 568/25; 568/33; 568/67; 568/630; 568/633; 568/640; 568/641; 568/651
[58] Field of Search ............ 568/25, 67, 630, 631, 568/633, 636, 640, 654, 23, 33, 651

[56] References Cited

U.S. PATENT DOCUMENTS

| | | | |
|---|---|---|---|
| 3,322,813 | 5/1967 | Seki et al. | 568/634 |
| 3,660,499 | 5/1972 | Kobayashi et al. | 568/634 |
| 3,686,331 | 8/1972 | O'Brien et al. | 568/634 |
| 3,830,849 | 8/1974 | Martin et al. | 568/634 |
| 3,896,042 | 7/1975 | Anderson et al. | |
| 3,950,328 | 4/1976 | Karrer | 568/630 |
| 4,141,921 | 2/1979 | Karrer | 568/635 |
| 4,186,141 | 1/1980 | Torii et al. | 568/613 |
| 4,226,800 | 10/1980 | Picklesimer | 568/630 |
| 4,338,468 | 7/1982 | Farooq et al. | 568/637 |
| 4,356,329 | 10/1982 | Bettarini et al. | 568/637 |
| 4,496,771 | 1/1985 | Massardo et al. | 568/651 |
| 4,540,711 | 10/1985 | Bettarini et al. | |
| 4,613,703 | 9/1986 | Hefner, Jr. | 568/640 |

OTHER PUBLICATIONS

IBM Technical Disclosure Bulletin, Vol. 27, issued Sep. 4, 1984, P.J. Brock et al., "Laminating Resin Compositions" see pp. 79, and 2529–2530.

Charles M. Starks et al., "Phase Transfer Catalysis Principles and Techniques", published 1978, by Academic Press (New York). See pp. 1–8, 57–63 and 77–78.

Primary Examiner—Werren B. Lone

[57] ABSTRACT

A process for preparing an aromatic propargyl ether, preferably bispropargyl ether, from phenolic compounds comprising vigorously stirring a propargyl halide, preferably propargyl chloride, with a phenolic compound, such as bisphenol A, in an aqueous sodium hydroxide solution at a temperature of from about 0° C. to about 100° C., in the presence of a phase transfer catalyst such as tetrabutylammonium bromide. The mixture is then filtered to recover a solid product. That product is washed with water and propanol. This process provides a product having greater than 98% purity in yields ranging from 85 to 97% of theoretical.

30 Claims, No Drawings

PROCESS FOR MAKING PROPARGYL ETHERS OF BISPHENOLS

BACKGROUND OF THE INVENTION

1. Related Application

This application is a continuation-in-part of U.S. patent application Ser. No. 056,190, filed June 1, 1987, hereby incorporated by reference.

2. Field of the Invention

The invention is related to the synthesis of aromatic propargyl ethers. More particularly, the present invention provides a process for preparing propargyl ethers derived from phenolic compounds.

Propargyl ethers are a class of acetylene-terminated monomers which show great promise for use in the preparation of thermoset resins with excellent properties.

3. Discussion of the Prior Art

U.S. Pat. No. 3,594,175 to Allan S. Hay, discloses producing dipropargyl ethers by reacting dihydric phenol with a propargyl halide in the presence of a base, e.g., alkali metal and alkaline earth metal hydroxides, carbonates, bicarbonates, etc. Because an alkali metal hydroxide reacts with the phenol to produce a salt of the phenol, the preformed alkali metal salt of the dihydric phenol can also be used. The propargyl ether product is purified by recrystallization.

U.S. Pat. No. 4,226,800 to Picklesimer, reports a process wherein a phenolic material is reacted with propargyl bromide in aqueous sodium hydroxide solution. The process suffers from the disadvantage of providing both O-propargylated (desired) and C-propargylated (undesired) materials. For example, bisphenol A is claimed to provide 45.4% yield of the desired bispropargyl ether and 43.6% yield of the undesired C-propargylated bisphenol. Additionally, the process employs rather vigorous conditions, such as reflux conditions of 100° C. for from 1 to 3 hours. A further drawback of the process is that propargyl bromide is used rather than propargyl chloride. The bromide is relatively expensive, inaccessible on a commercial scale, and shock sensitive according to Fire Technology, 5, 100 (1969).

The present invention overcomes deficiencies of the prior art mentioned above, which is hereby incorporated by reference.

SUMMARY OF THE INVENTION

In view of the above prior art problems and limitations, it is desirable to prepare propargyl ethers from hydroxyaromatic compounds by means of a suitable process utilizing less expensive and safe reagents under mild conditions.

It is another object of the present invention to prepare propargyl ethers from hydroxyaromatic materials in dilute aqueous caustic solution at ambient temperatures.

It is another object of the present invention to prepare propargyl ethers from hydroxyaromatic compounds combined with propargyl chloride.

It is another object of the present invention to prepare propargyl ethers directly in excellent purity and high yields to avoid recovering the propargyl ethers by recrystallization.

The present invention overcomes deficiencies of the prior art mentioned above.

The present invention concerns a process for preparing a propargyl ether of a hydroxyaromatic compound which process comprises contacting a hydroxy aromatic compound with a propargyl halide in an aqueous solution of an alkaline agent in the presence of a phase transfer catalyst under reaction conditions sufficient to produce the propargyl ether of the hydroxyaromatic compound.

If desired, the propargyl ether of hydroxyaromatic compound when formed as a solid can be filtered out of the reaction solution. The solid product can then be washed with water and an alcohol such as methanol, ethanol, isopropanol and the like to recover 95 to 100 percent of a theoretical yield of the propargyl ether compound having a purity greater than 95 percent.

Alternatively, the product when formed as a liquid can be extracted into an organic solvent such as methylene chloride, ethyl acetate, ethyl ether and the like and recovered after removal of the solvent.

The present invention differs from the above processes in that small amounts of a phase transfer catalyst, such as tetraalkylammonium halide is used which enables the reaction to be carried out in dilute aqueous, caustic solution at ambient temperatures within a few hours. Surprisingly, the present invention can use propargyl chloride rather than the bromide. This will lead to less hazardous situations during scale-up. An even more surprising finding is that the process provides the propargyl ethers directly in excellent purity (greater than 95%) and in high yields of at least 80%, preferably 85–97%, without significant contamination of the carbon-alkylated materials, as reported in U.S. Pat. No. 4,226,800. This finding is indeed remarkable because there are reports of C-alkylated materials as by products during the phase transfer-catalyzed alkylation of phenols with the related allyl and benzyl halides according to E. D'Incan et P. Viout, *Tetrahedron*, 31, 159 (1975).

This invention relates to a process for preparing a propargyl ether comprising the steps of reacting a phenolic compound with propargyl halide in an aqueous solution of an alkaline agent in the presence of a phase transfer catalyst under reaction conditions sufficient to produce the propargyl ether.

This invention also relates to a process for preparing a propargyl ether comprising the steps of:

reacting a bisphenol A with propargyl chloride in an aqueous sodium hydroxide solution in the presence of tetrabutylammonium bromide at a temperature from about 20° to about 50° C., a mole equivalent ratio of the bisphenol A to the propargyl chloride from 1:2 to 1:3, a mole equivalent ratio of the bisphenol A to the tetrabutylammonium bromide from 1:0.005 to 1:0.05, a mole equivalent ratio of the bisphenol A to the sodium hydroxide from 1:2 to 1:4, for a reaction time of 4 to 16 hours to produce the propargyl ether;

filtering the propargyl ether out of the solution to produce a solid product; and washing the solid product with water and isopropanol to recover 95 to 100% of a theoretical yield of the propargyl ether, the washed propargyl ether having a purity greater than 98%.

DETAILED DESCRIPTION OF THE INVENTION

Hydroxyaromatic compounds employed in the present invention are aromatic compounds having one or more hydroxyl groups per molecule. The hydroxyaromatic compounds may bear groups or substituents which do not interfere with the reaction of the present invention. These hydroxyaromatic compounds can be monocyclic or polycyclic aromatic compounds. Polycyclic aromatic compounds can have two or more aromatic ring nuclei which are (a) connected to each other by a direct bond, (b) connected to each other by a suitable bridging group, or (c) fused to each other. These hydroxyaromatic compounds are generally represented by the following formulae:

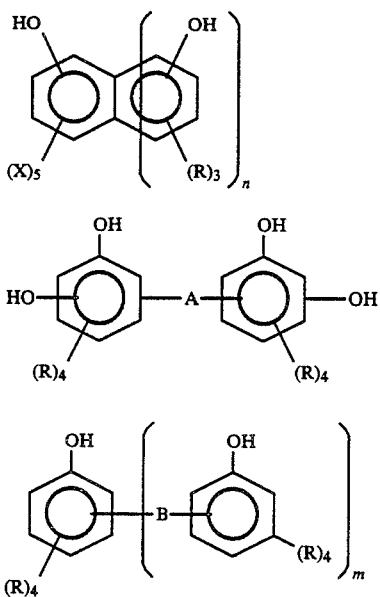

wherein A is a direct bond, —O—, —S—, —SO—, —S$_2$—, —CO—, a divalent hydrocarbon radical, a divalent halogen substituted hydrocarbon radical, or a divalent cycloaliphatic radical; B is independently in each occurrence a divalent hydrocarbon radical, X is independently in each occurrence hydrogen, an alkyl radical, an alkoxy radical, an aryl radical, an aryloxy radical; R is independently in each occurrence hydrogen, an alkyl radical, an alkoxy radical, hydroxy, or halogen; n is 0, 1 or 2; and m is an integer of from 1 to 100, preferably an integer of from 1 to 10, most preferably 5 to 10.

The divalent hydrocarbon radicals contemplated by A and B in the foregoing formulae contain from 1 to 12 carbon atoms and can be branched or unbranched radicals. These radicals can also be substituted with one or more aromatic hydrocarbon radicals having from 6 to 12 carbon atoms, such as phenyl, biphenyl, bisphenyl, naphthyl and the like. Preferably, the divalent hydrocarbon radical contains from 1 to 8 carbon atoms most preferably from 1 to 4 carbon atoms. Examples of preferred divalent hydrocarbon radicals are methylene, 1,2-ethylene, 1,1-ethylene, 1,3-propylene, 1,2-propylene, 2,2-propylene, 1,4-butylene, diphenylmethylene, phenylmethylene etc.

The divalent halogen substituted hydrocarbon radicals contemplated by A in the foregoing formulae are bromo-, chloro-, fluoro- and iodo-substituted hydrocarbon radicals having from 1 to 12, preferably 1 to 8, most preferably 1 to 4 carbon atoms. Preferred halogen-substituted hydroxycarbon radicals are fluoroalkylene radicals having from 1 to 4 carbon atoms. The most preferred is 2,2-perfluoropropylene (—C(CF$_3$)$_2$—).

The divalent cycloaliphatic radicals contemplated by A in the foregoing formulae contain from 8 to 20 carbon atoms, preferably 8 to 12 carbon atoms, most preferably 8 to 10 carbon atoms. Dicyclopentadienyl radical is particularly preferred divalent cycloaliphatic radical. This radical is represented by the following formula:

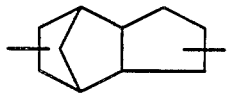

IV

The alkyl radicals contemplated by X and R in the foregoing formulae are straight and branched chain radicals having from 1 to 12 carbon atoms. Preferably the alkyl radicals contain from 1 to 8 carbon atoms, most preferably 1 to 4 carbon atoms. Examples of these alkyl radicals are methyl, ethyl, propyl, butyl, pentyl, heptyl, octyl, nonyl, decyl, undecyl, dodecyl and the branched chain isomers thereof.

The alkoxy radicals contemplated by X and R in the foregoing formula are straight and branched chain radicals having from 1 to 12 carbon atoms, preferably 1 to 8 carbon atoms, most preferably 1 to 4 carbon atoms. Examples of these radicals are methoxy, ethoxy, propoxy, butyloxy, pentyloxy, hexyloxy, heptyloxy, octyloxy, nonyloxy, decyloxy, undecyloxy, dodecyloxy and the branched chain isomers thereof.

Halogens contemplated by X and R in the foregoing formula are bromine, chlorine, fluorine and iodine. Chlorine and bromine are preferred halogens.

The aryl radicals contemplated by X in the foregoing formulae contains from 6 to 14 carbon atoms, preferably from 6 to 10 carbon atoms. Examples of the aryl radicals are phenyl, naphthyl and anthracyl. Phenyl is the most preferred aryl radical.

The aryloxy radicals contemplated by X in the foregoing formulae contain from 6 to 14 carbon atoms preferably from 6 to 10 carbon atoms. Examples of the aryloxy radicals are phenoxy, naphthyloxy and anthracyloxy. The most preferred aryloxy radical is phenoxy radical.

The preferred hydroxyaromatic compounds of formula I are those in which n is 0. The most preferred are those in which n is 0, four X substituents are hydrogens and one X is 4-phenoxy, 3-methyl or 4-methyl.

The preferred hydroxyaromatic compounds of formula II are those in which the two hydroxyl groups are in the 4 and 4' positions. These compounds are commonly referred to as bisphenols. Particularly suitable bisphenols include for example, bisphenol A, hexafluorobisphenol A, bisphenol F, bisphenol S, bisphenol K, tetrabromobisphenol A, tetrabromobisphenol F, tetrabromobisphenol K, and tetrabromobisphenol, wherein the bromine atoms are in meta position to the hydroxyl and the like group.

The preferred hydroxyaromatic compounds of formula III are phenol novolac and resorcinol novolac resins having, respectively the repeating units represented by the following formulae:

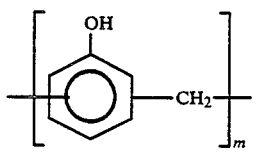

V

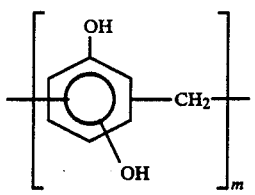

wherein m is defined as hereinbefore.

Propargyl halides suitably employed in the practice of this invention are represented by formula VII as follows:

    VII wherein Y is chlorine, bromine or iodine. Preferred propargyl halides are propargyl chloride and propargyl bromide. The most preferred propargyl halide is propargyl chloride. For every one mole equivalent of phenolic material, the present invention employs 1 to 1.5 mole equivalents of the propargyl halide, preferably 1 to 1.15 mole equivalents of the propargyl halide.

An alkaline agent is used in the practice of the present invention for the purpose of increasing conversion to the propargyl ether. For example, the alkaline agent may be an alkaline metal hydroxide or an alkaline earth metal hydroxide. Preferred alkaline agents are potassium hydroxide, sodium hydroxide or mixtures thereof. Sodium hydroxide is the most preferred alkaline agent. For every 1 mole equivalent of hydroxyaromatic compound about 1 to about 10 mole equivalents of caustic solution are used, preferably about 2 to about 4 mole equivalents of caustic solution.

Water is typically used in the process of the present invention for the purpose of solubilizing transient phenate salts and co-produced alkali or alkaline earth metal salts. Water facilitates resolution of the bisphenol ether products from water soluble catalysts, coproduced salts, and residual alkaline agent, if any. Generally, from about 1 to about 20 moles of water will be used per mole of hydroxyaromatic reactant. Using more than this amount of water is disadvantageous because of the reduced rate of the overall reaction. The use of excess water requires more energy to maintain a given elevated reaction temperature. Using less water than the previously indicated minimum is disadvantageous because it may result in inadequate mixing and dissolution of the reactants as well as inadequate separation of the propargyl ether product.

A phase transfer catalyst is used in the process of the present invention. It is critical to the process. It is used for the purpose of providing unexpected yields of propargyl ether product at higher conversion of the hydroxy aromatic reactants to the desired product. The purity of the product resulting from selectivity of the catalyst are unexpected. In many cases, the catalyst speeds the rate of reaction and improves and speeds the dissolution of transient phenate salts. Suitable catalysts are (a) quarternary ammonium, phosphonium or arsonium salts, (b) poly(ethylene glycols), (c) poly(ethylene glycol alkylethers), (d) macrocyclic polyethers commonly known as crown ethers, and (e) cryptates.

Quarternary ammonium, phosphonium or arsonium salts are represented by formula VIII.

    VIII wherein Z is a tetravalent ammonium or phosphonium or arsonium ion, A is any suitably counter ion, and each $R_1$, $R_2$, $R_3$ and $R_4$ is independently an alkyl, arylalkyl, aromatic or alkyaromatic moiety containing from 1 to 50 carbon atoms, preferably 1 to 12 carbon atoms, most preferably 1 to 6 carbon atoms. Examples of these moieties are methyl, ethyl, propyl, butyl, pentyl, hexyl, heptyl, octyl, nonyl, decyl, undecyl, dodecyl phenyl, naphthyl, toyl, xylyl, benzyl and the like.

Tetravalent ammonium ions are the preferred Z cations in formula VIII. Typical A counter ions include chloride, bromide, fluoride, iodine and hydroxyl ions. Iodide and bromide are the preferred A counter ions. Quaternary ammonium halides are the preferred catalysts. Tetraalkylammonium halides where the sum of the number of carbon atoms in the alkyl groups $R_1$, $R_2$, $R_3$ and $R_4$ is 16 or less, and benzyl trialkylammonium halides, such as benzyl trimethyl ammonium halides, are the most preferred catalysts. Any effective amount of catalyst may be used. It must be sufficient to catalyze the reaction. Typically, 0.001 to 0.1 mole equivalent of phase transfer catalyst is used per mole equivalent of hydroxy-aromatic reactant. From about 0.005 to about 0.05 mole equivalents of phase transfer catalyst is preferred. Most preferably about 0.02 to 0.05 mole equivalents is used.

Catalytic quaternary ammonium, phosphonium, or arsonium salts may be bound in a polymeric support in the form of ionexchange resins. Typical ion-exchange resins are those which bear quaternary ammonium salts on macroporous styrene-divinyl benzene resins. Examples of these bound quarternary salts include DOWEX MSA-1 and the like. DOWEX is a registered trademark. The ion-exchange resin form of catalyst is advantageous in that it is easily recovered or, if used in a fixed bed, obviates the need for a catalyst recovery step. It should be noted that a catalyst bound in a polymeric support does not go into solution when used according to the method of the present invention. When solid particles of bound catalyst are used, it is preferred that they be dispersed uniformly in the reaction mixture or form a fixed bed.

The poly(ethylene glycol) that may be used as a phase transfer catalyst in the present invention has the formula $H(OCH_2CH_2)_nOH$ and a molecular weight ranging from about 200 to about 50,000.

The poly(ethylene glycol alkyl ether) that may be used as a phase transfer catalyst in the present invention has the formula:

$R(OCH_2CH_2)_nOH$ wherein R is an alkyl group having 1 to 50 carbon atoms and the ether has a molecular weight ranging from about 200 to about 50,000.

The crown ether that may be used as a catalyst in the present invention is a macrocyclic polyether whose structure exhibits a conformation with a so-called hole capable of trapping cations by coordination with a lone pair of electrons on the oxygen atoms. An example of a crown ether is 15-crown-5 shown as follows:

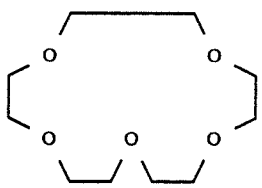

Other examples are shown in the text *Phase Transfer Catalysts*, C. M. Starks, C. Liotta, page 78, Academic Press (1978), hereby incorporated by reference. Suitable crown ether catalysts include 18-crown-6, dicyclohexane-18-crown-6, dibenzyl-18-crown-6, 15-crown-5, and the like.

Cryptates, that the present invention may use, are macrobicyclic ethers having the following general formula:

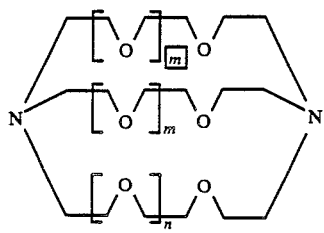

When $m=0$ and $n=1$, this is a 2.1.1 cryptate. When $m=1$ and $n=0$, this is a 2.2.1 cryptate. When $m=n=1$ this is a 2.2.2 cryptate. Phase transfer catalysts are further discussed by *Phase Transfer Catalysts*, C. M. Starks, C. Liotta, Academic Press (1978).

Reactants may be combined in any order. However, it is preferred to add the hydroxy aromatic reactant to a mixture of water, alkaline agent and catalyst, and to add the propargyl halide as the last component. It is equally preferred to add the hydroxy aromatic reactant and the catalyst first, followed by the alkaline agent and water, then followed by the propargyl halide.

The reaction is typically conducted at a temperature of from about 0° to about 100° C. at atmospheric pressure, preferably from about 20° to about 50° C. At temperatures below 0° C. the reaction proceeds more slowly. Temperatures greater than 100° C. may be used but may lead to catalyst instability, which is undesirable. If a temperature greater than 100° C. is used, pressures higher than atmospheric pressure should then be used to reduce the loss of water and propargyl halide.

The reaction time is a function of temperature, type and concentration of catalyst and the concentration of the hydroxy aromatic reactant. The reaction to form the propargyl ether typically takes between about 2 and about 12 hours.

When the reactants, alkaline agent, catalyst and water are properly combined under reaction conditions as herein specified, a product mixture will be formed. At least one component of the product mixture will contain a propargyl group and will correspond structurally to the particular hydroxy aromatic reactant used as a starting material. The products formed are generally represented by the formulas IX and X when derived from the products having formulas I, II and III, respectively:

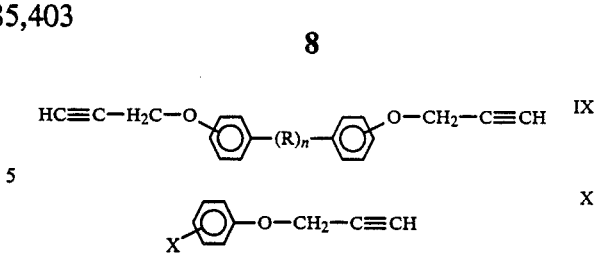

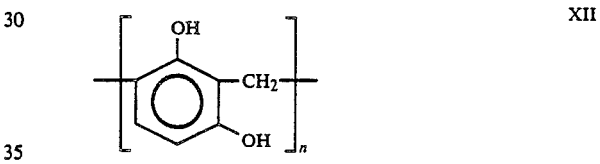

Various polyhydric phenolic materials can be utilized in conducting the process of this invention. Examples of such materials include mononuclear, polyhydric phenols, such as resorcinol, hydroquinone, 2,3-dicyanohydroquinone, and the like, as well as polyhydric, polynuclear phenols, also known as (bi)phenols. It is preferred to use 4,4'-dihydroxy diphenol-sulfone and 4,4'-isopropylidenediphenol (bisphenol A).

It is also within the scope of the invention to utilize phenolic resins, such as phenol novolac and resorcinol novolac resins having, respectively the following Formulas XI and XII:

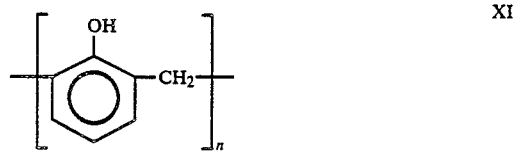

In Formulas XI and XII, n is an integer ranging from about 2 to about 100. It is generally preferred to use a resin in which n ranges from 5 to 10.

The present invention has the advantages in that small amounts of a phase transfer catalyst enable the reaction to be carried out in dilute aqueous caustic solution at ambient temperatures within a few hours. Surprisingly, it can use propargyl chloride, rather than the bromide (although the latter works equally well). This leads to less hazardous situations during scale-up. An even more surprising finding is that the process provides the propargyl ethers directly in excellent purity (greater than 98%) and in high yields of at least 80%, preferably 85 to 97% of theoretical yield without significant contamination of the carbon-alkylated materials, as reported in U.S. Pat. No. 4,226,800. This finding is indeed remarkable because there are reports of C-alkylated materials as by-products during the phase transfer-catalyzed alkylation of phenols with the related allyl and benzyl halides (e.g., E. D'Incan et P. Viout, *Tetrahedron*, 31, 159 (1975)). Also, U.S. Pat. No. 4,613,703 to Hefner, Jr., hereby incorporated by reference, discloses producing an isomeric mixture of C— and O— allylated aromatic compounds by contacting an allyl halide, a hydroxy aromatic reactant, an alkaline agent, and water in the presence of a phase transfer catalyst.

The products prepared by the process of the present invention can be converted to polymers by thermal polymerization of the acetylene groups. The polymers obtained are useful as adhesives and matrix resins in the fabrication of composites. Because volatile by-products are not evolved during the polymerization, the composites are free of undesirable voids.

A more complete understanding of the invention can be obtained by referring to the following illustrative examples which are not intended, however, to limit the invention.

Comparative Example A

This example illustrates the general procedure used in Example 1 of U.S. Pat. No. 3,594,175 for the preparation of the di-propargyl ethers of di-hydric phenols. A solution of 1 mole of 4,4'-isopropylidenediphenol(bisphenol A) (228 grams) in two liters of acetone is reacted with 2.4 moles of propargyl bromide (284 grams) in the presence of 2.4 moles of potassium carbonate (332 grams), by heating under reflux for 12 to 48 hours. After filtering the reaction mixture, the filtrate is evaporated to dryness on a steam bath. The residue is dissolved in diethyl ether and extracted with 5% potassium hydroxide and then washed with water. After removal of the diethyl ether, the residue is recrystallized from methanol. This recovered a 75% yield of bisphenol A bispropargyl ether represented by the following formula:

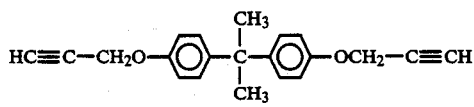

Comparative Example B

This example illustrates the general procedure used in U.S. Pat. No. 4,226,800 in which a run is conducted using bisphenol A as the phenolic material. See Example VII. The amounts of the materials used are as follows:

TABLE 1

| Bisphenol A | 228 grams, 1.0 mole |
|---|---|
| Propargyl bromide | 238 grams, 2.0 moles |
| Sodium hydroxide | 80 grams, 2.0 moles |

The bisphenol A and sodium hydroxide are dissolved in 1 liter of water in a reaction flask. The propargyl bromide is added in one addition as an 80% solution in toluene. The mixture is heated rapidly to reflux temperature and refluxed for 2.5 hours. The aqueous phase is neutral at this point, indicating completion of the reaction. The product is separated as a dark resinous liquid by means of a separatory funnel. Toluene is permitted to evaporate. The product is extracted with 500 milliliters of 2-propanol. The 2-propanol insoluble material is dried and weighed 138.0 grams (45.4% yield). U.S. Pat. No. 4,226,800 teaches that the product is bispropargyl ether of bisphenol A as indicated by a melting point of 84°-85° C. and infrared spectra. The 2-propanol-soluble component is recovered in 43.6% yield, and the infrared spectra confirmed the presence of propargyl groups as well as hydroxyl groups. The two recovered products are represented by the following formula:

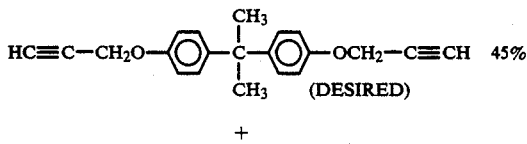

45% (DESIRED)

+

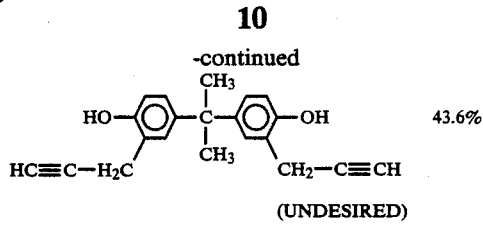

43.6%

(UNDESIRED)

Thus, the process of U.S. Pat. No. 4,226,800 suffers from the disadvantages of providing both O-alkylated (desired) and C-alkylated (undesired) materials. For example, bisphenol A is claimed to provide 45.4% yield of the desired bispropargyl ether and the balance is the unwanted C-propargylated bisphenol. Additionally, the process employs rather vigorous conditions such as reflux temperatures of 100° C. for two and one-half hours. A further drawback of the process is that propargyl bromide is employed rather than propargyl chloride.

EXAMPLE 1

The following illustrates the general method of the present invention. 45.6 grams of bisphenol A (0.2 moles), 200 milliliters of 20% aqueous sodium hydroxide, and 3.22 grams of tetrabutylammonium bromide (0.01 moles) are combined at 20° C. To this mixture at 20° C., 34.7 grams of propargyl chloride (0.46 moles) is added over a 10 minute period, and the mixture is stirred overnight at room temperature for 16 hours. This produced white crystals that are filtered, washed two times with 200 milliliters of water and two times with 50 milliliters of isopropanol. This produced the desired bispropargyl ether. This bispropargyl ether weighed, after drying, 57.9 grams, for a yield of 95.2 weight percent. Also it had a melting point of 83° C. and a purity, measured by gas chromatograph, of 99.7%.

The bispropargyl ether produced is represented by the following formula:

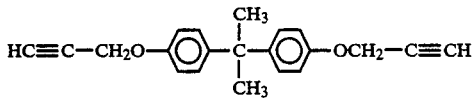

Due to the high purity of the product, no recrystallization is necessary to recover it.

EXAMPLE 2

Example 1 is repeated. However the reactants are stirred at 50° C. for a period of 4 hours, and 2 to 5 mole percent of tetrabutyl ammonium bromide is used as the phase transfer catalyst. This produced an 85 to 97% yield of bispropargyl ether having greater than 98% purity. Accordingly, no recrystallization is necessary to recover the bispropargyl ether.

EXAMPLE 3

Example 1 is repeated except bisphenol A is replaced by bisphenol S (4,4'-dihydroxydiphenyl sulfone). The bispropargyl ether of bisphenol S is recovered as light tan crystals, mp 184°-186° C., yield 96.2%. The product is further characterized by proton magnetic resonance spectroscopy (pmr). Solvent (DMSO —$d_6$)$\delta$7.92 (d,4H,J=8.3 Hz), 7.16 (d, 4H, J=8.3 Hz), 4.86 (d, 4H, J=2.2 Hz) and 3.58 (t, 2H, J=2.2 Hz).

The recovered bispropargylether of bisphenol S is represented by the following formula:

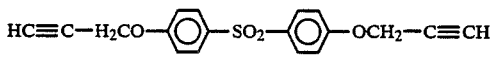

EXAMPLE 4

Example 1 is repeated except bisphenol A is replaced by bisphenol K (4,4'-dihydroxy benzophenone). The bispropargyl ether of bisphenol K is obtained as off-white crystals, mp 79°–81° C., yield 95.6%. Pmr data: CDCl$_3$ solvent, $\delta$7.84 (d, 4H, J=8.4 Hz), 7.20 (d, 4H, J=8.4 Hz), 4.76 (d, 4H, J=2.2 Hz) and 2.58 (t, 2H, J=2.2 Hz). The recovered bispropargyl ether of bisphenol K is represented by the following formula:

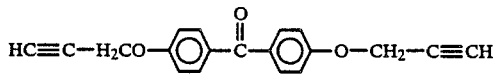

EXAMPLE 5

Example 1 is repeated except bisphenol A is replaced by bisphenol F. The bispropargyl ether is extracted with ethyl acetate and recovered as viscous brown oil with an isolated yield of 98.7% and $G_c$ purity of 98.2%. Pmr data: CDCl$_3$ solvent, 720 (d, 4H, J=9 Hz), 6.95 (d, 4H, J=9 Hz), 4.66 (d, 4H, J=2.2 Hz), 3.88 (S, 2H, CH$_2$) and 2.54 (t, 2H, J=2.2 Hz). The recovered bispropargyl ether of bisphenol F is represented by the following formula:

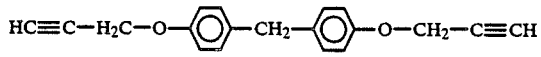

EXAMPLE 6

Example 1 is repeated except bisphenol A is replaced by 4,4'-thiodiphenol. The bispropargyl ether is obtained as brown oil and recovered by extraction with ethyl acetate. The product has an isolated yield of 96% and a purity of 98% as shown by $G_c$. Pmr data: CDCl$_3$ solvent, $\delta$7.28 (d, 4H, J=8.2 Hz), 6.88 (d, 4H, J=8.2 Hz), 4.62 (d, 4H, J=2.2 Hz) and 2.49 (t, 2H, J=2.2 Hz). The recovered bispropargylether of thio diphenol B is represented by the following formula:

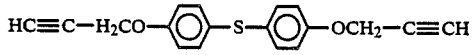

EXAMPLE 7

97.5 gms of hexafluorobisphenol A (0.29 mol). 350 ml of 20% aqueous sodium hydroxide and 4.8 gms of tetrabutylammonium bromide (0.015 mol) are combined at 20° C. To this mixture is added 59.6 grams of propargyl chloride (0.8 mol) and the mixture is heated at 45°–50° C. for 5 hours. The mixture is cooled, diluted with 200 ml of water and the product is extracted with ethyl acetate (300 ml). The organic solution is dried (MgSO$_4$) and evaporated to recover the bispropargyl ether of hexafluorobisphenol A as a viscous, brown liquid (113.4 grams, 94.8%). $G_c$ purity is found to be 98.6%. Pmr data: CDCl$_3$ solvent, $\delta$7.40 (d, 4H, J=8.5 Hz), 7.05 (d, 4H, J=8.5 Hz), 4.80 (d, 4H, J=2.15 Hz) and 2.68 (t, 2H, J=2.2 Hz). The recovered bispropargylether of hexafluoro bisphenol A is represented by the following formula:

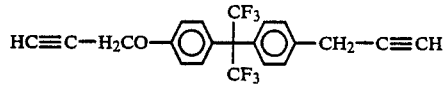

EXAMPLE 8

Example 7 is repeated except hexafluorobisphenol A is replaced by 4,4'-oxydiphenol. The bispropargyl ether of 4,4'-oxydiphenol is recovered as a brown, oily liquid in 97% yield and 97.6% $G_c$ purity. Pmr data: / $\delta$6.86 (m, 8H, aromatic, 4.58 (d, 4H, J=2.2 Hz), 2.48 (t, 2H, J=2.2 Hz). The recovered bispropargyl ether of 4,4'-oxydiphenol is represented by the following formula:

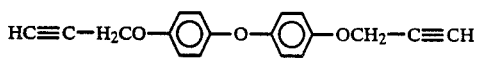

EXAMPLE 9

Example 7 is repeated except hexafluorobisphenol A is replaced by 4,4'-dihydroxybiphenyl. The bispropargyl ether is recovered as an off-white powder in 98.8% yield and a $G_c$ purity of 97%. Pmr data: DMSO—d$_6$ solvent, $\delta$7.78 (d, 4H, J=8.5 Hz), 7.24 (d, 4H, J=8.5 Hz), 4.92 (d, 4H, J=2.2 Hz) and 3.62 (t, 2H, J=2.2 Hz). The recovered bispropargyl ether of 4,4'-dihydroxybisphenyl is represented by the following formula:

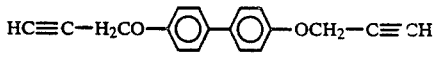

EXAMPLE 10

Example 7 is repeated except hexafluorobisphenol A is replaced by 1,7-dihydroxynaphthalene. The bispropargyl ether of 1,7-dihydroxynaphthalene is recovered as a viscous semi-solid in 91% yield. Pmr data: CDCl$_3$ solvent, $\delta$7.8–6.6 (m 6H, aromatic), 4.78 (d, 4H, J=2.2 Hz), 2.51 (t, 2H, J=2.2 Hz). The bispropargyl ether of 1,7-dihydroxynaphthalene is represented by the following formula:

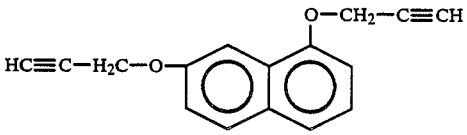

EXAMPLE 11

Example 7 is repeated except hexafluorobisphenol A is replaced by tris (4-hydroxyphenyl) methane. 3.6 equivalents of propargyl chloride is used in this experiment. The trispropargyl ether is recovered as yellow crystals in 90% yield. Pmr data: CDCl$_3$ solvent, $\delta$6.70 (m, 12H, aromatic), 5.18 (S, 1H CH), 4.56 (d, 6H, J=2.2 Hz) and 2.50 (t,4H, J=2.2 Hz). The bispropargyl ether of tris(4-hydroxyphenyl) methane is represented by the following formula:

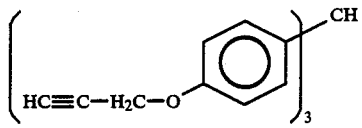

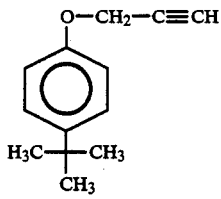

EXAMPLE 12

Example 7 is repeated except hexafluorobisphenol A is replaced by DCPD-phenol Novalac. The propargyl ether is recovered as brown viscous syrup in 98% yield. PMR data: solvent $CDCl_3$, $\delta 7.50$–$6.52$ (m 8H, aromatic), 4.64 (m, 4H) 2.44 (m,2H) and 2.40–0.7 (m, 14H). The recovered bispropargyl ether of DCPD-novolac is represented by the following formula:

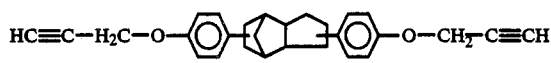

EXAMPLE 13

Example 7 is repeated except hexafluorobisphenol A is replaced by phenol-formaldehyde-novalac resin (n=7). The propargyl ether is recovered in 94.5% yield, is characterized by pmr spectral data, and has the repeating units represented by the following formula:

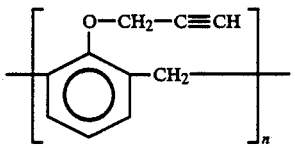

EXAMPLE 14

A mixture of p-cresol (100 g, 0.926 mol), propargyl chloride (85.7 g, 0.115 mol), 20% NaOH (400 ml) and tetrabutylammonium iodide (11.10 g, 0.03 mol) is vigorously agitated at ambient temperature for 30 hrs. The product propargyl ether is recovered after dilution with 500 ml water and extraction with 500 ml methylene chloride. The propargyl ether of p-cresol is recovered as yellow liquid in 99% yield which is distilled and characterized by pmr spectroscopy. The recovered propargyl ether of p-cresol is represented by the following formula:

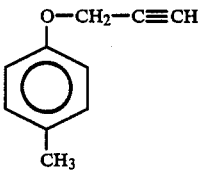

EXAMPLE 15

Example 14 is repeated except that p-cresol is replaced by 4-t-butylphenol. The product, 4-t-butylphenyl propargyl ether, is isolated as a colorless liquid in 98% yield and characterized by pmr spectroscopy. The product is represented by the following formula:

EXAMPLE 16

A solution of potassium hydroxide (85%, 2.3 gms, 0.035 mol) in 15 ml water, 2.28 gms of bisphenol A (0.01 mol) and 0.166 gm of tetrabutylammonium bromide (0.0005 mol) are combined at 20° C. To this stirred mixture at 20° C. is added propargyl chloride (1.8 gms, 0.024 mol) and the mixture is stirred at room temperature for 24 hours. This produces the desired bispropargyl ether of bisphenol A as colorless solid which is filtered, washed with water followed by isopropanol. The product weighs 2.86 gms after drying (94.5 yield) and melts at 82°–83° C. $G_c$ purity is found to be 99.4%

EXAMPLE 17

Example 16 is repeated except potassium hydroxide is replaced by lithium hydroxide (0.040 mol). 2.92 gms of the bispropargyl ether of bisphenol A (96%) is isolated as in experiment 16.

EXAMPLE 18

Example 1 is repeated except propargyl bromide (as a solution in toluene) is used instead of propargyl chloride. The desired bispropargyl ether of bisphenol A is isolated in 94.9% yield. The product has a melting point of 83° C. and exhibits consistent pmr spectral data.

EXAMPLE 19

The results of several experiments wherein a number of different phase transfer catalysts have been used in the dipropargylation of bisphenol A are given in Table I. The results clearly indicate that a wide range of catalysts are effective for the preparation of propargyl ethers in 20% aqueous caustic solution at room temperature.

TABLE 2

Phase Transfer Catalyzed Dipropargylation of Bisphenol A Under Conditions as Cited in Example 1.

| Experiment | Catalyst | % Isolated Yield of bispropargyl ether |
|---|---|---|
| 1. | Tetraethylammonium bromide | 94.5 |
| 2. | Tetramethylammonium iodide | 93.8 |
| 3. | Tricaprylylmethylammonuium chloride | 91.2 |
| 4. | Benzyltrimethylammonium bromide | 95.1 |
| 5. | Tetrabutylphosphonium bromide | 94.8 |
| 6. | DOWEX MSA-1 chloride form (5 gms resin) | 97.6 |
| 7. | Polyethylene glycol methyl ether [MW = 350] | 96.5 |
| 8. | Polyethylene glycol [MW = 400] | 94.8 |

Although the invention has been described in conjunction with specific embodiment, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for preparing a propargyl ether comprising the step of:

reacting a hydroxy aromatic compound with a propargyl halide having the formula HC≡C—CH$_2$X, where X is Cl, Br or I, in an aqueous solution of an alkaline agent in the presence of phase transfer catalyst, being quarternary salt, poly(ethylene glycol), poly(ethylene glycol alkylether), macrocyclic polyether or cryptate under reaction conditions sufficient to produce the propargyl ether directly in excellent purity and in high yields without significant contamination of carbon alkylated materials.

2. The process of claim 1, wherein the phase transfer catalyst is a quaternary salt represented by the following formula:

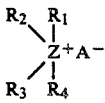

wherein Z is a tetravalent ammonium, arsonium or phosphonium ion, A is a suitable counterion, and each R$_1$, R$_2$, R$_3$ and R$_4$ is independently an alkyl, aromatic or alkyl aromatic moiety containing from 1 to about 50 carbon atoms, polyethylene glycol ethers having a molecular weight from about 200 to about 50,000, crown ethers, or cryptates, the reacting step producing at least 80% of a theoretical yield of the propargyl ether.

3. The process of claim 2, wherein the propargyl halide is propargyl chloride or propargyl bromide.

4. The process of claim 3, wherein the alkaline agent comprises sodium hydroxide, potassium hydroxide, lithium hydroxide or mixtures thereof.

5. The process of claim 4, wherein reaction conditions comprise reacting the phenolic compound at a temperature from about 0° to about 100° C.

6. The process of claim 5, wherein the reaction conditions further comprise a mole equivalent ratio of the phenolic compound to the phase transfer catalyst from 1:0.001 to 1:0.1.

7. The process of claim 6, wherein the reaction conditions further comprise a mole equivalent ratio of the phenolic compound to the alkaline agent from 1:1 to 1:10.

8. The process of claim 7, wherein the phase transfer catalyst is tetraalkylammonium halide.

9. The process of claim 8, wherein the hydroxy aromatic compound has the following formula:

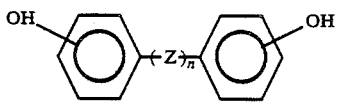

wherein Z is CO, SO, SO$_2$, O, S, C(CF$_3$)$_2$ or C(CH$_3$)$_2$ and n is 0 or 1.

10. The process of claim 8, wherein the hydroxy aromatic compound has the following formula:

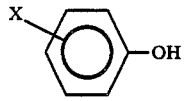

wherein X is 4-OPh, 3-Me or 4-Me.

11. The process of claim 8, wherein the hydroxy aromatic compound is a polyhydic mononuclear phenol.

12. The process of claim 8, wherein the hydroxy aromatic compound is a phenolic novolac resin.

13. The process of claim 9, wherein the number of carbon atoms in the alkyl groups R$_1$, R$_2$, R$_3$ and R$_4$ is 16 or less.

14. The process of claim 13, wherein the propargyl halide is propargyl chloride.

15. The process of claim 14, wherein the catalyst is a tetravalent ammonium ion and the A counterion is bromide.

16. The process of claim 15, wherein the reaction conditions further comprise a mole equivalent ratio of the hydroxy aromatic compound to the propargyl chloride from 1:2 to 1:3.

17. The process of claim 16, wherein the reaction conditions further comprise a mole equivalent ratio of the phenolic compound to the phase transfer catalyst from 1:0.005 to 1:0.05.

18. The process of claim 17, wherein the alkaline agent is sodium hydroxide.

19. The process of claim 18, wherein the reaction conditions further comprise a mole equivalent ratio of the phenolic material to the sodium hydroxide from 1:2 to 1:4.

20. The process of claim 19, wherein the reaction conditions further comprise reacting the hydroxy aromatic compound and the propargyl chloride at a temperature from about 20° to about 50° C.

21. The process of claim 20, wherein the hydroxy aromatic compound is bisphenol A.

22. The process of claim 21, wherein the reaction conditions further comprise a reaction time from about 4 to about 16 hours.

23. The process of claim 22, wherein the catalyst is bound in a polymeric support.

24. The process of claim 23, wherein the reaction conditions further comprise a mole equivalent ratio of the hydroxy aromatic compound to the phase transfer catalyst from about 1:0.02 to about 1:0.05.

25. The process of claim 1, further comprising filtering the propargyl ether from the solution to produce a solid product and washing the solid product with water and isopropanol to recover 85 to 95% of a theoretical yield of the propargyl ether, the washed propargyl ether having a purity of greater than 98%.

26. A process for preparing a propargyl ether comprising the steps of:

reacting a bisphenol A with propargyl chloride in an aqueous sodium hydroxide solution in the presence of tetrabutylammonium bromide at a temperature from about 20° to about 50° C., a mole equivalent ratio of the bisphenol A to the propargyl chloride from 1:2 to 1:3, a mole equivalent ratio of the bisphenol A to the tetrabutylammonium bromide from 1:0.005 to 1:0.05, a mole equivalent ratio of the bisphenol A to the sodium hydroxide from 1:2 to 1:4, to produce the propargyl ether;

filtering the propargyl ether from the solution to produce a solid product; and washing the solid product with water and isopropanol to recover 95 to 100% of a theoretical yield of the propargyl ether, the washed propargyl ether having a purity greater than 98%.

27. The process of claim 1, wherein the hydroxy aromatic compound has the following formulae:

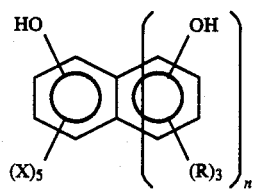
(I)

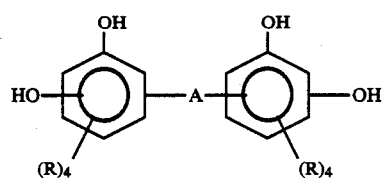
(II)

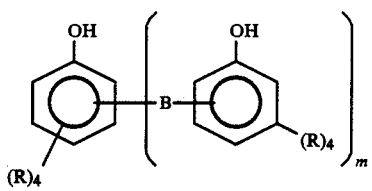
(III)

wherein A is a direct bond, —O—, —S—, —SO—, —S$_2$—, —CO—, a divalent hydrocarbon radical, a divalent halogen substituted hydrocarbon radical, or a divalent cycloaliphatic radical; B is independently in each occurrence a divalent hydrocarbon radical, X is independently in each occurrence hydrogen, an alkyl radical, an alkoxy radical, an aryl radical, an aryloxy radical; R is independently in each occurrence hydrogen, an alkyl radical, and alkoxy radical, hydroxy, or halogen; n is 0, 1 or 2; and m is an integer of from 1 to 100.

28. The process of claim 27, wherein m is an integer from 1 to 10.

29. The process of claim 28, wherein me is an integer from 5 to 10.

30. The process of claim 1, wherein the alkyline agent is an alkyline metal hydroxide or an alkyline earth metal hydroxide.

* * * * *

UNITED STATES PATENT AND TRADEMARK OFFICE
CERTIFICATE OF CORRECTION

PATENT NO. : 4,885,403

DATED : December 5, 1989

INVENTOR(S) : Muthiah N. Inbasekaran and Stoil K. Dirlikov

It is certified that error appears in the above-identified patent and that said Letters Patent is hereby corrected as shown below:

Column 6, line 36, "ionexchange" should read --ion-exchange--.

Column 10, line 27, "34.7" should read --34,27--; line 33, "This" should read --The--.

Column 11, line 27, "720" should read --7.20--; line 68, "2.2" should read --2.15--.

Column 12, line 14, "/" should read --CDCl$_3$ solvent,--; line 15, "d,4H" should read --4H, d--; line 65, "4.56" should read --4.45--.

Column 14, Table 2, "Tricaprylylmethylammonuium" should read --Tricaprylylmethylammonium--.

Signed and Sealed this

Twenty-first Day of April, 1992

Attest:

HARRY F. MANBECK, JR.

*Attesting Officer*  *Commissioner of Patents and Trademarks*